United States Patent
Hoeg (10) Patent No.: US 9,572,478 B2
(45) Date of Patent: Feb. 21, 2017

(54) SWING PRISM ENDOSCOPE

(75) Inventor: Hans David Hoeg, Arcadia, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1116 days.

(21) Appl. No.: 12/180,138

(22) Filed: Jul. 25, 2008

(65) Prior Publication Data
US 2010/0022838 A1   Jan. 28, 2010

(51) Int. Cl.
| | | |
|---|---|---|
| A61B 1/04 | (2006.01) | |
| A61B 1/06 | (2006.01) | |
| F16H 35/08 | (2006.01) | |
| A61B 1/00 | (2006.01) | |
| G02B 23/18 | (2006.01) | |
| A61B 1/005 | (2006.01) | |

(52) U.S. Cl.
CPC ......... *A61B 1/00096* (2013.01); *A61B 1/0052* (2013.01); *A61B 1/00066* (2013.01); *A61B 1/00183* (2013.01); *G02B 23/18* (2013.01)

(58) Field of Classification Search
CPC .................................................. G02B 23/18
USPC ........ 600/106, 107, 131, 170–171, 173–174; 359/211.2; 385/36; 74/25, 56, 89, 839
See application file for complete search history.

(56) References Cited

U.S. PATENT DOCUMENTS

| | | | |
|---|---|---|---|
| 1,726,268 A | 8/1929 | Jahr | |
| 2,292,082 A * | 8/1942 | Miller | .............................. 236/10 |
| 2,987,960 A | 6/1961 | Sheldon | |
| 3,417,745 A * | 12/1968 | Sheldon | ........................ 600/167 |
| 3,804,081 A | 4/1974 | Kinoshita et al. | |
| 3,818,902 A * | 6/1974 | Kinoshita et al. | ............ 600/109 |
| 3,856,000 A | 12/1974 | Chikama | |
| 3,871,365 A | 3/1975 | Chikama | |
| 3,880,148 A | 4/1975 | Kanehira et al. | |
| 3,896,793 A | 7/1975 | Mitsui et al. | |
| 4,569,333 A * | 2/1986 | Bel | ..................... A61B 1/00188 600/163 |
| 4,697,577 A | 10/1987 | Forkner | |
| 5,575,757 A * | 11/1996 | Kennedy | ............ A61B 1/00188 600/167 |

(Continued)

FOREIGN PATENT DOCUMENTS

| | | |
|---|---|---|
| EP | 0251478 B1 | 8/1991 |
| GB | 2354836 A | 4/2001 |

(Continued)

OTHER PUBLICATIONS

Extended European Search Report; EP 09 16 6294; Oct. 15, 2009; 7 pages.

*Primary Examiner* — Ryan Henderson
*Assistant Examiner* — Aaron B Fairchild
(74) *Attorney, Agent, or Firm* — Whitmyer IP Group LLC (57) ABSTRACT

A swing prism endoscope with an actuating mechanism that comprises a control element that oscillates in between proximal and distal ends of the endoscope and is coupled to a distally mounted swing prism, a control surface with a variable profile, and an engaging element that contacts the control surface and moves relative to the control surface while contacting the control surface causing the control element to oscillate. The distally mounted swing prism that alters the viewing angle of the endoscope between a forward direction that is substantially parallel to the longitudinal axis of the endoscope and a side direction that is angled relative to the longitudinal axis of the endoscope.

31 Claims, 4 Drawing Sheets

(56) References Cited

U.S. PATENT DOCUMENTS

| | | | |
|---|---|---|---|
| 5,762,603 A | 6/1998 | Thompson | |
| 5,836,867 A * | 11/1998 | Speier | A61B 1/00188 600/112 |
| 5,978,161 A * | 11/1999 | Lemke | A61B 1/00188 359/824 |
| 6,110,105 A | 8/2000 | Durell | |
| 6,364,830 B1 | 4/2002 | Durell | |
| 6,371,909 B1 | 4/2002 | Hoeg et al. | |
| 6,500,115 B2 | 12/2002 | Krattiger et al. | |
| 6,522,477 B2 * | 2/2003 | Anhalt | A61B 1/00096 600/112 |
| 6,537,210 B1 * | 3/2003 | Wulfsberg | 600/173 |
| 6,560,013 B1 | 5/2003 | Ramsbottom | |
| 6,616,602 B1 * | 9/2003 | Witte | 600/167 |
| 6,638,216 B1 | 10/2003 | Durell | |
| 6,648,817 B2 | 11/2003 | Schara et al. | |
| 6,817,976 B2 * | 11/2004 | Rovegno | 600/173 |
| 6,929,603 B2 | 8/2005 | Durell | |
| 6,932,760 B1 * | 8/2005 | Pang | A61B 1/04 600/133 |
| 2003/0092966 A1 | 5/2003 | Schara et al. | |
| 2003/0097044 A1 | 5/2003 | Rovegno | |

FOREIGN PATENT DOCUMENTS

| | | |
|---|---|---|
| JP | 62284626 A | 12/1987 |
| JP | H07327916 A | 12/1995 |
| JP | 2004255200 A | 9/2004 |
| JP | 2005334275 A | 12/2005 |
| JP | 2007509710 A | 4/2007 |
| WO | 2005041755 A2 | 5/2005 |
| WO | 2005122868 A1 | 12/2005 |

* cited by examiner

SWING PRISM ENDOSCOPE

FIELD OF THE INVENTION

The present invention relates to variable direction of view endoscopes, in particular, rigid shaft endoscopes with swing prisms mounted at the distal end.

BACKGROUND OF THE INVENTION

Variable direction of view endoscopes allow the user to change the endoscopic viewing direction without having to change the position of the endoscope itself. Variable direction of view endoscopes come in two general classes: rigid and flexible. Such endoscopes are useful when the user wants to see structures which are beside or behind the tip of the endoscope but can not easily move the endoscope shaft because of anatomical constraints or constraints imposed by other surgical instruments in the operative field.

Variable direction endoscopy is desirable because it affords surgeons greater flexibility in their procedural approach. Increased viewing mobility improves the quality of diagnoses, as in cystoscopy for example, where a typical diagnostic screening involves inspecting the interior surface of the bladder for lesions or tumors. The ability to look laterally and retrograde is important when doing this type of diagnosis because it makes it possible to visually cover the entire bladder surface, including the entrance region near the bladder neck. In ear-nose-throat and neurosurgical procedures, variable viewing is desired because the procedures are delicate, and the entrance ports are small. It is therefore not possible to manipulate the endoscope significantly without injuring the patient. The ability to look sideways and backwards is important however during and after tumor resection when it is necessary to keep track of tumor fragments, which if not caught can nucleate new tumors. Laparoscopy, another surgical discipline, imposes fewer maneuvering constraints but still benefits markedly from variable direction viewing because it allows surgeons to get better observation angles during a procedure and increases diagnostic capabilities. Also, because of the greater viewing versatility, variable direction of view endoscopes can minimize conflicts with other tools and can simplify surgical planning by their ability to achieve standard viewing angles from nonstandard positions, allowing the surgeon to keep the endoscope "off to the side" but still get the desired view.

A fundamental feature of variable direction endoscopy is that it generally makes it possible for surgeons to eliminate "blind movements." A blind movement is the process of moving an instrument inside a patient without being able to see where the instrument is heading. This can occur when it is necessary to advance a fixed-angle side viewing endoscope in its length direction without being able to see what is ahead of the scope, or when a surgical tool has to be manipulated at the boundary of the endoscopic field of view.

Generally, rigid scopes are easier for surgeons to control than flexible scopes. This is because there is a rigid connection between the tip of the endoscope and the surgeon's hand. When the surgeon moves her hand, the movement of the proximal end of the scope translates directly to the distal end of the scope, and it is easy for the user to develop a mental picture of how the scope tip moves based on her hand movement. This is not true of flexible endoscopes where the dynamic relationship between the distal and proximal ends of the scope is not always obvious. For this reason, use of flexible endoscopes often requires substantial training, and therefore many surgeons prefer rigid scopes if the situation permits.

Rigid and flexible scopes are typically designed for different applications, and they are not interchangeable. While flexible scopes have been widely adopted in the medical marketplace, rigid variable direction of view scopes have yet to establish themselves. A number of rigid variable direction of view endoscopes have been presented over the years, all with the goal of providing the surgeon with improved viewing mobility over traditional fixed-angle endoscopes. They have achieved this goal, but unfortunately their drawbacks have outweighed their advantages. For a given diameter the image quality delivered by a rigid variable direction of view endoscope is generally not as good as that delivered by a fixed-angle endoscope because some of the optical channel must be sacrificed in favor of the actuation mechanism, which also limits the field of view. The actuation mechanism adds complexity and cost to the design, manufacturing and assembly processes. The added mechanical complexity in turn reduces robustness and makes sterilization more difficult. Further, making variable direction of view endoscopes ergonomic and user-friendly is challenging. In several surgical disciplines, especially laparoscopy, it is necessary for the surgeon to be able to hold the endoscope flat across the patient's body in order to access certain parts of the anatomy. This practice requires that the endoscope have a minimal handle which is generally symmetric about the main axis of the endoscope. Therefore, gun-grip type handles are not suitable for surgical applications.

Another significant problem with current variable direction of view endoscopes (flexible or rigid with flex tip) is disorientation. As the endoscopic line of sight is changed, the user faces two difficulties. The first is keeping track of where the endoscope is "looking." With a rigid fixed-angle endoscope it is relatively easy for the user to extrapolate the endoscopic viewing direction from the position of the endoscope shaft. This is not the case when the viewing direction is regularly changed relative to the longitudinal axis of the endoscope; the user quickly loses track of spatial orientation within the anatomy being observed. The second difficulty is keeping track of what is "up" in the endoscopic image. Depending on the view-changing mechanism, the image will rotate relative to the surroundings, and the user frequently loses orientation. This disorientation is often not correctable, especially in variable direction of view scopes which have distal imagers and no facility for changing image orientation.

Given the difficulties of variable direction endoscopes, it is common for surgeons to utilize rigid endoscopes with fixed viewing angles. Surgeons rely heavily on knowing that a certain endoscope provides a 30 or 45 degree viewing angle. This preference for using multiple fixed angle endoscopes is due in part to the fact that a surgeon knows that for a particular endoscope they can dependably know what the anatomy should look like.

What is desired, therefore, is a variable direction of view endoscope with an actuation mechanism that reduces the complexity and cost of the device while also providing a device that is robust and provides for ease of sterilization. What is further desired is an actuation mechanism that minimizes the amount of optical channel that is sacrificed for the mechanism. What is also desired is a variable view endoscope that is ergonomic to improve the handling and ease of use of the device. What is still further desired is a variable view endoscope that assists the surgeon in maintaining spatial orientation when altering the viewing angle.

SUMMARY OF THE INVENTION

Accordingly, it is an object of the present invention to provide a swing prism endoscope with a control element that is displaced axially in between proximal and distal ends of the endoscope and is coupled to a distally mounted swing prism such that the axial displacement of the control element induces the swing prism to rotate about a prism axis, a control surface with a variable profile, and an engaging element that contacts the control surface and moves relative to the control surface while contacting the control surface causing the swing prism to oscillate. The engaging element can be formed on a drive element that rotates about a longitudinal axis of the endoscope. Alternatively, the control surface can be formed on a drive element that rotates about a longitudinal axis of the endoscope.

It is another object of the invention for the variable profile of the control surface to comprise a peak that corresponds to a maximum viewing angle of the swing prism and a trough that corresponds to a minimum viewing angle of the swing prism.

It is a further object of the invention for the engaging element or control surface to be magnetically coupled to a prism adjusting knob, the movement of which induces a corresponding movement of either the engaging element or control surface. The prism adjusting knob can be radially disposed above the engaging element or the control surface and rotate about the longitudinal axis of the endoscope.

It is yet another object of the invention for the endoscope to comprise a handle that also encompasses the longitudinal axis of the endoscope and is adjacent to the prism adjusting knob such that the endoscope can be grasped and the prism adjusting knob rotated with a single hand.

It is further object of the invention for the rotation of the prism adjusting knob to have a 1:1 correspondence to the change of the viewing angle of the swing prism.

It is also beneficial if the endoscope comprises at least one preset viewing angle such that when the prism adjusting knob is rotated to the preset viewing angle, the prism adjusting knob is secured at that location. In one embodiment, the prism adjusting knob comprises an orientation element that extends along the longitudinal axis of the endoscope and engages a portion of the endoscope that encompasses the longitudinal axis of the endoscope and comprises a receiving element at the preset viewing angle that receives and secures the orientation element at that location.

It is still a further object of the invention for the endoscope to comprise a distally mounted swing prism that alters the viewing angle of the endoscope between a forward direction that is substantially parallel to the longitudinal axis of the endoscope and a side direction that is angled relative to the longitudinal axis of the endoscope. When the swing prism is oriented with a viewing angle in the forward direction, the swing prism conveys a light image to transmittal optics or a solid state imager without substantially altering the image direction. When the swing prism is oriented with a viewing angle in the side direction, the swing prism reflects a light image to transmittal optics or a solid state imager by altering the image direction from a first direction to a second direction. In a preferred embodiment, the swing prism is a dove prism.

It is yet another object of the invention for the swing prism to be disposed within a housing that comprises a viewing window that spans the forward and side view angles. It is preferred that the portion of the viewing window that spans the forward and side view angles comprises a spherical arc.

Other objects of the invention and its particular features and advantages will become more apparent from consideration of the following drawings and accompanying description.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 1:
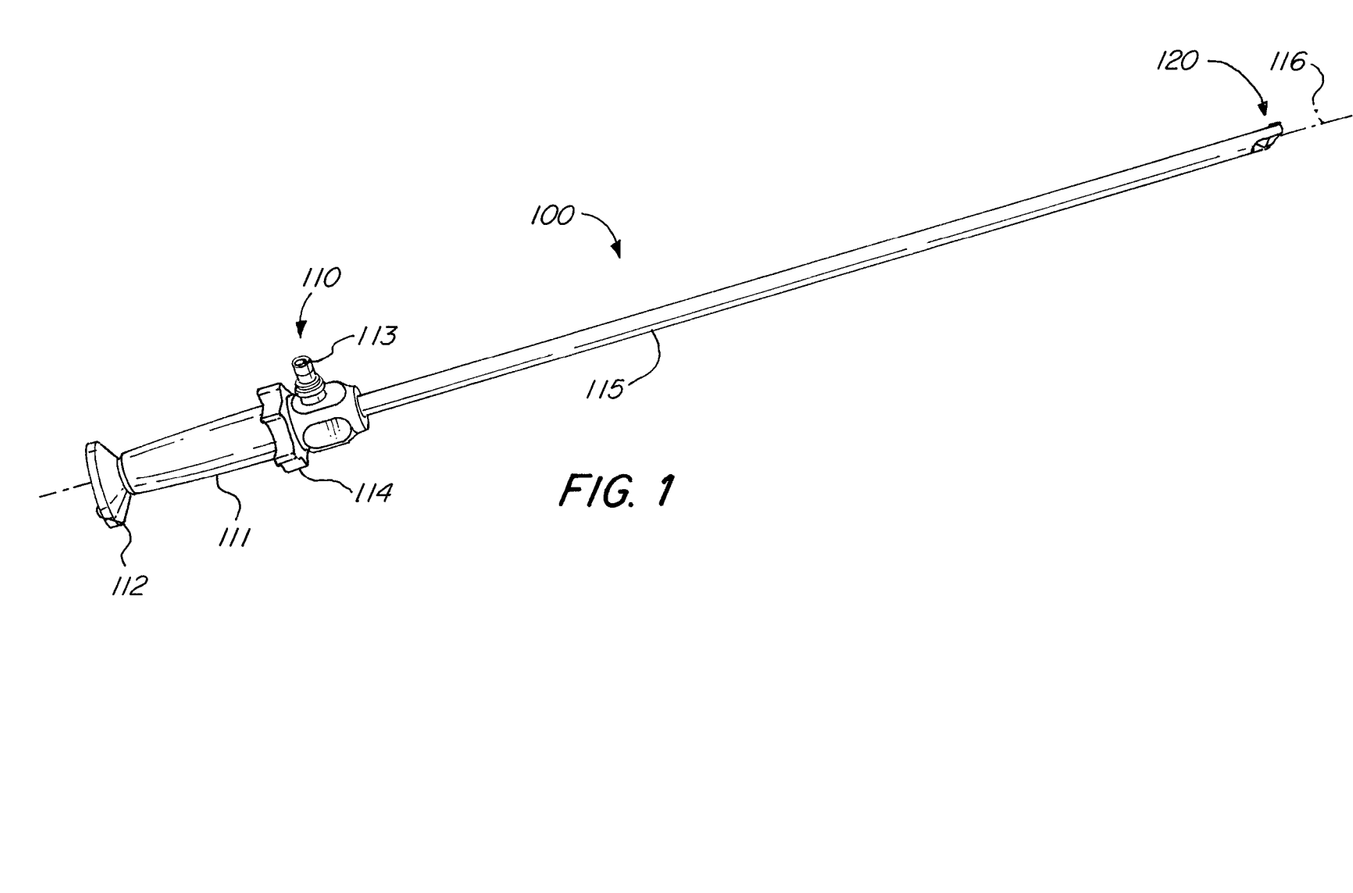
FIG. 1 is a perspective view of the swing prism endoscope of the present invention.

FIG. 1 illustrates a variable direction of view endoscope 100 with a rigid shaft 115 extending from a proximal end 110 to a distal end 120. Endoscope 100 comprises a central axis 116 that is encompassed by the components of the endoscope. When the distal end 120 is inserted in to a body cavity, light source adapter 113 conveys light from the proximal end 110 to the distal end 120 of the endoscope enabling light to be projected in to the cavity from the distal end. The distal end 120 comprises a swing prism that rotates about a prism axis and receives an image of the cavity. Optical components in rigid shaft 115 convey the image from the distal end 120 to the proximal end 110. To view the image received by the swing prism, a surgeon secures endoscope 100 by grasping handle 111, which encompasses central axis 116, and views the cavity through eye piece 112. Alternatively, a camera, known to one skilled in the art, can be attached to eye piece 112 or replace eye piece 112, such that the cavity can be viewed on a video monitor.

Since the swing prism rotates about a prism axis, the surgeon is able to change the viewing angle of the endoscope without altering the orientation of the endoscope within the body cavity. While grasping handle 111, the surgeon is able to use the same hand to rotate prism adjusting knob 114 about central axis 116, which in turn induces the swing prism to rotate about the prism axis and changes the angle that the swing prism receives a light image relative to the axis 116 of endoscope 110. Manipulation of the swing prism with one hand is facilitated by the fact that the handle 111 and prism adjusting knob 114 are disposed adjacent to one another and both encompass central axis 116. By disposing the handle and adjusting knob about the axis of the endoscope and placing these elements adjacent to one another, the endoscope provides an improved ergonomic device that eases the use of the endoscope by a surgeon.

Figure 2A:
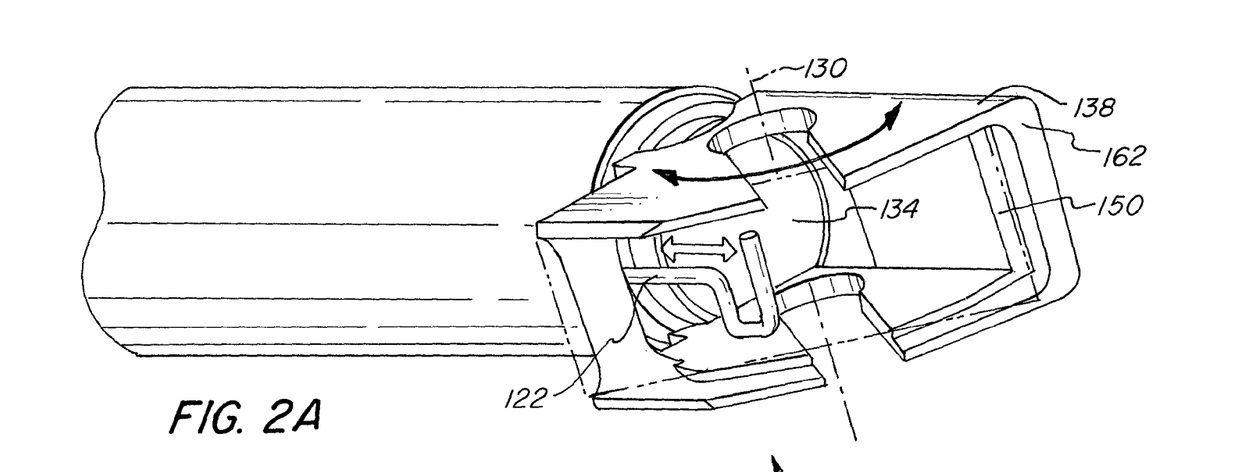
FIG. 2A is a perspective view of the distal end of the swing prism endoscope of the present invention with the distal portion of the outer housing removed.
Figure 2B:
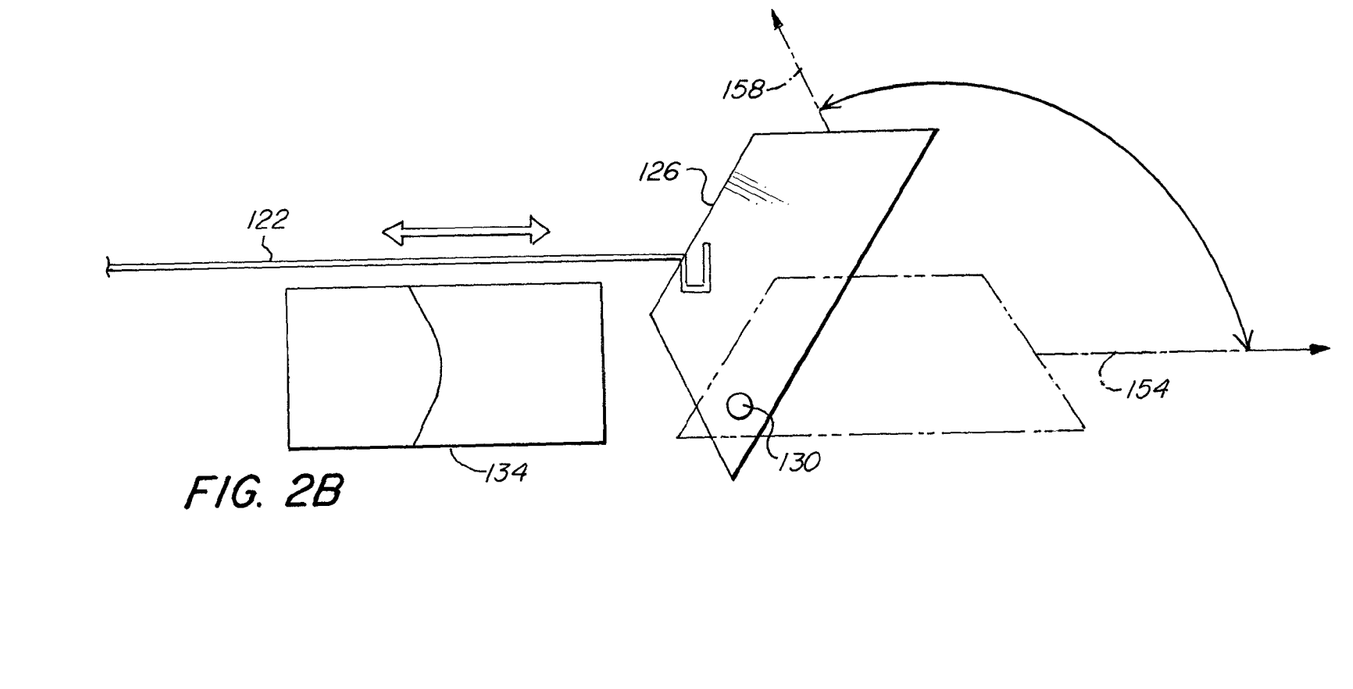
FIG. 2B is a schematic view of the distal end of the swing prism endoscope of the present invention depicting a swing prism, transmittal optics, and an activating wire.

FIGS. 2A and B provide a more detailed view of the distal end 120 of endoscope 100. As shown in these figures, the rotation of dove prism 126 about prism axis 130 is induced by a wire 122 that is coupled to the prism. Wire 122 extends from the proximal end 110 to the distal end 120 and is coupled to prism adjusting knob 114 in a manner discussed in more detail below. The rotation of prism adjusting knob 114 induces wire 122 to move in the proximal or distal directions and consequently cause the dove prism 126 to rotate about the prism axis 130.

In the particular embodiment shown in FIGS. 2A and B, dove prism 126 is able to rotate the viewing angle between zero degrees 154 in the forward direction and 120 degrees 158 in the side direction relative to central axis 116. Dove prism 126 is characterized by the fact that when oriented at zero degrees 154, dove prism 126 does not alter the course of the image, such that the image is transmitted straight through the prism 126 to transmittal optics 134. When dove prism 126 is oriented in the side direction, the prism alters the course of the image towards transmittal optics 134 enabling side views to be transmitted to the eye piece 112. Alternatively, a solid state imager, such as a CCD or CMOS imager, can replace or be integrated with the transmittal optics. In such an embodiment, the imaging surface of the solid state imager can be placed at the distal end and oriented normal to the central axis of the endoscope. The imaging surface can either receive an image from the transmittal optics or directly from the dove prism. A dove prism is beneficial because it provides a simplified mechanism for directing an image to transmittal optics, i.e. it can illuminate the need to provide multiple mirrors or prisms for redirecting an image. As a result, the simplified mechanism enables the diameter of the distal end of the endoscope to be reduced. The dove prism is also beneficial because a single prism can facilitate viewing in the forward, side and backward directions (>90 degrees).

To enable dove prism 126 to be secured within endoscope 100, distal housing 138 is provided at distal end 120 adjacent to transmittal optics 134 and incorporates a cavity that receives dove prism 126. Distal housing 138 is characterized by a curved surface 162, which can be in the form of a spherical arc (i.e. the section of a sphere), and a ledge 150 that receives a corresponding curved viewing window, not shown, which can also be in the form of a spherical arc. When the viewing window is spherically shaped, the optical properties of the endoscope are enhanced, enabling the endoscope to maintain high image quality throughout viewing range of swing prism 126. At least a portion of the curved viewing window is shaped such that the length, width and contour of the window correspond to the dimensions of ledge 150 and the portion of the curved window is encompassed by the portion of the housing 138 forming curved surface 162. By disposing viewing window on ledge 150, curved surface 162 can protect the viewing window from impacts that might otherwise damage the window.

In general, the manner in which adjusting knob 114 induces wire 122 to be displaced axially is achieved by coupling the wire to a control element that is displaced between the forward and backward direction, i.e. the control element is axially displaced in the direction of the proximal and distal ends of endoscope 100. While the drive element oscillates, the control element maintains its orientation relative to a longitudinal axis of the endoscope. Endoscope 100 further incorporates a variable surface and an engaging element. The variable surface has a profile that varies from the lateral perspective of endoscope 100, i.e. a portion of the variable surface extends in the distal direction. The engaging element contacts the variable surface and slides along the variable surface. In one embodiment, the variable surface can be maintained in a static orientation relative to the longitudinal axis while the engaging element moves relative to the variable surface. In another embodiment, the engaging element is maintained in a static orientation relative to the longitudinal axis while the variable surface moves relative to the engaging element. In either case, during the relative motion of these components to each other, the movement of the control element in the proximal direction is caused by the engaging element moving towards the portion of the variable surface extending towards the distal direction. The movement of the control element in the distal direction is caused by the engaging element moving away from the portion of the variable surface extending towards the distal direction. These elements provide an improved actuating mechanism for changing the viewing angle of an endoscope. This two element construction reduces the complexity of typical actuating mechanisms and enables the actuating mechanisms to provide predictable adjustments such that disorientation by a surgeon can be avoided.

FIGS. 3A-D depict a preferred embodiment of the mechanism by which the view angle of a swing prism is adjusted. Disposed within handle 111 is a control element 210 that encompasses the longitudinal axis of endoscope 100. Control element 210 comprises a variable surface 211 that is oriented towards the distal end of endoscope 100. The profile of variable surface 211 changes from the lateral perspective of endoscope 100 such that variable surface 211 comprises a trough portion 212 and a peak portion 213, which extends in the distal direction. A sloped transition region 214 extends from trough portion 212 to peak portion 213. Also disposed within handle 111 and opposite variable surface 211 is drive element 220, which also encompasses the longitudinal axis of endoscope 100 and rotates about this axis. Drive element 220 comprises an engaging element 221, which extends from drive element 220 in the proximal direction along the longitudinal axis and contacts variable surface 211. Encompassing drive element 220 is prism adjusting knob 230, which also rotates about the longitudinal axis. Prism adjusting knob 230 and drive element 220 are magnetically coupled, i.e. either the prism adjusting knob 230 or the drive element 220 contain a magnetic element such that the rotation of the prism adjusting knob 230 by a surgeon causes the drive element 220 to rotate in the same direction. Because of this magnetic coupling, the endoscope can be sealed and the knob kept completely external, allowing simpler cleaning and sterilization.

Contacting the proximal surface of control element 210 is spring 240. Spring 240 resides between control element 210 and spring retaining element 241. Spring 240 forces variable surface 211 against engaging element 221 ensuring that engaging element 221 remains in contact with variable surface 211 as the engaging element moves along variable surface 211.

In operation, a surgeon rotates prism adjusting knob 230 either clockwise or counter clockwise. The magnetic coupling of the prism adjusting knob 230 to the drive element 220 causes the drive element 220 to rotate in the same manner. The rotation of the drive element 220 causes the engaging element 221 to slide along variable surface 211. When the engaging element 221 slides towards peak portion 213, the control element 210 is displaced in the proximal direction. When the engaging element 221 slides towards trough portion 212, the control element is drawn towards the distal direction. While the drive element 220 rotates, the control element maintains its orientation relative to the longitudinal axis.

Figure 3A:
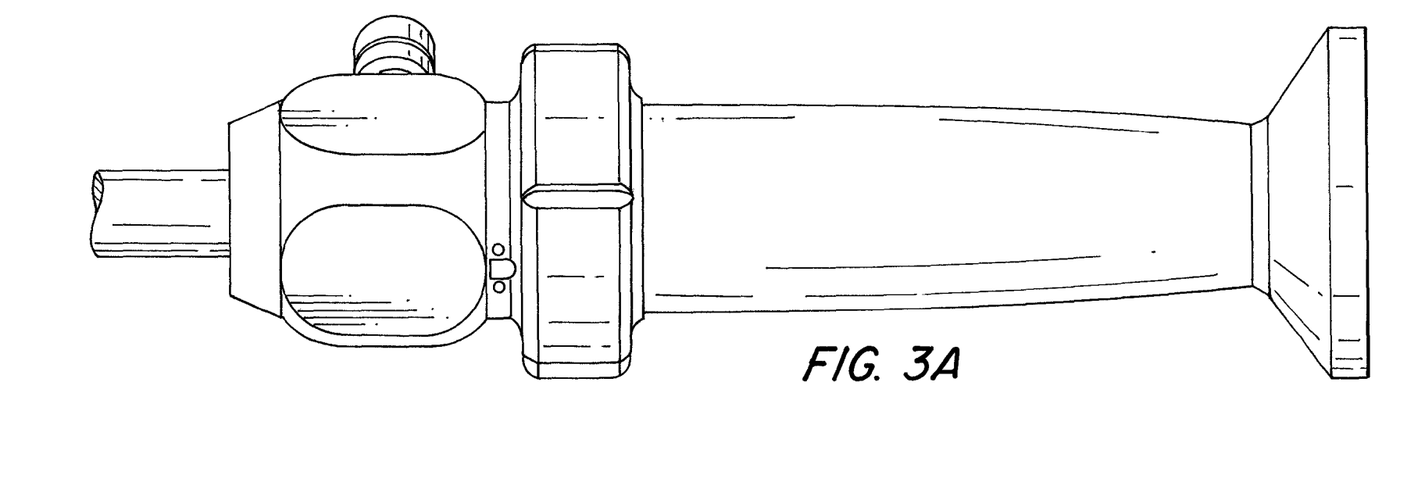
FIG. 3A is a side view of the proximal end of the swing prism endoscope of the present invention.
Figure 3B:
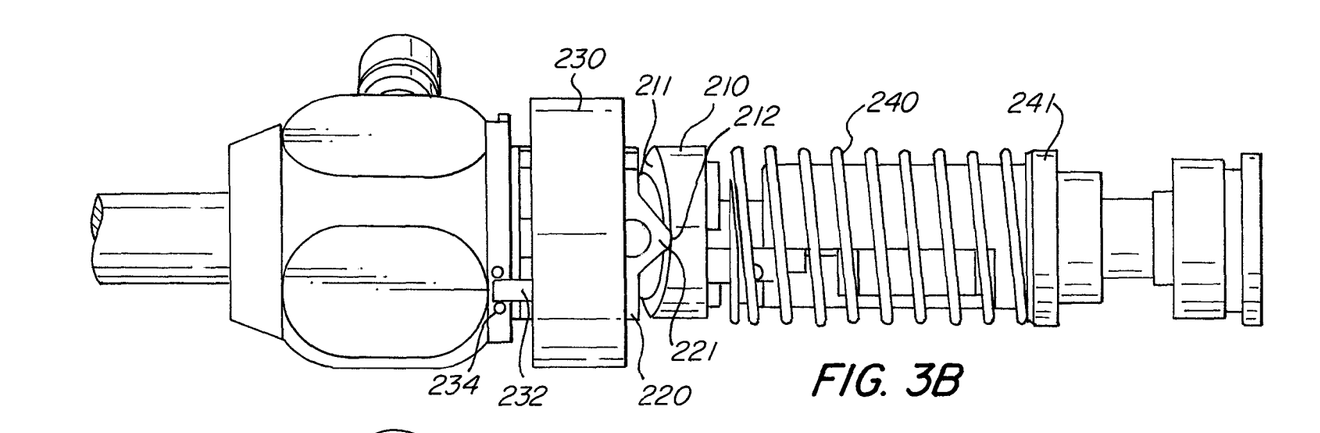
FIG. 3B is a side view of the proximal end of the swing prism endoscope of the present invention with the portion of the endoscope forming the handle removed.
Figure 3C:
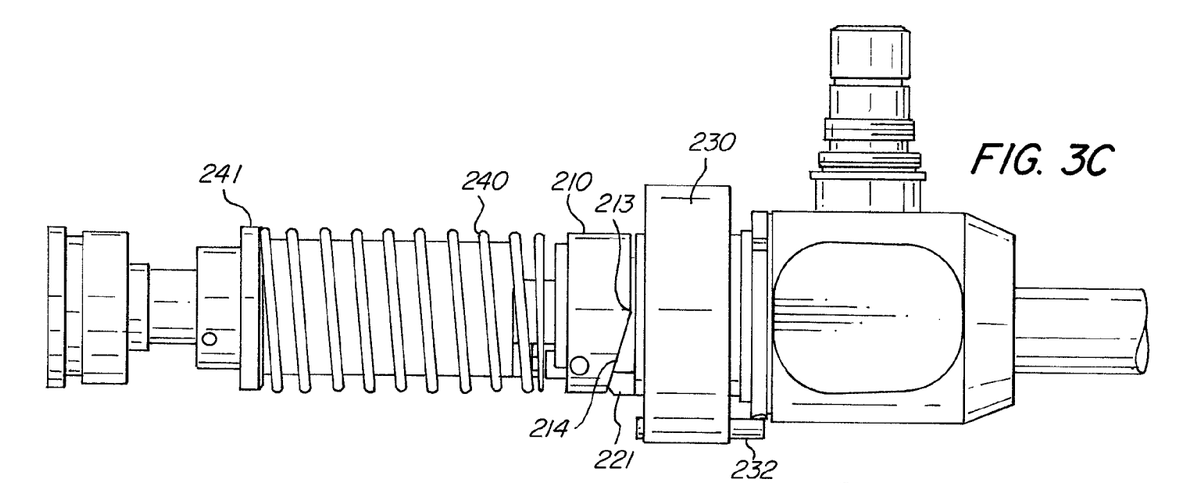
FIG. 3C is another side view of the proximal end of the swing prism endoscope of the present invention with the portion of the endoscope forming the handle removed.
Figure 3D:
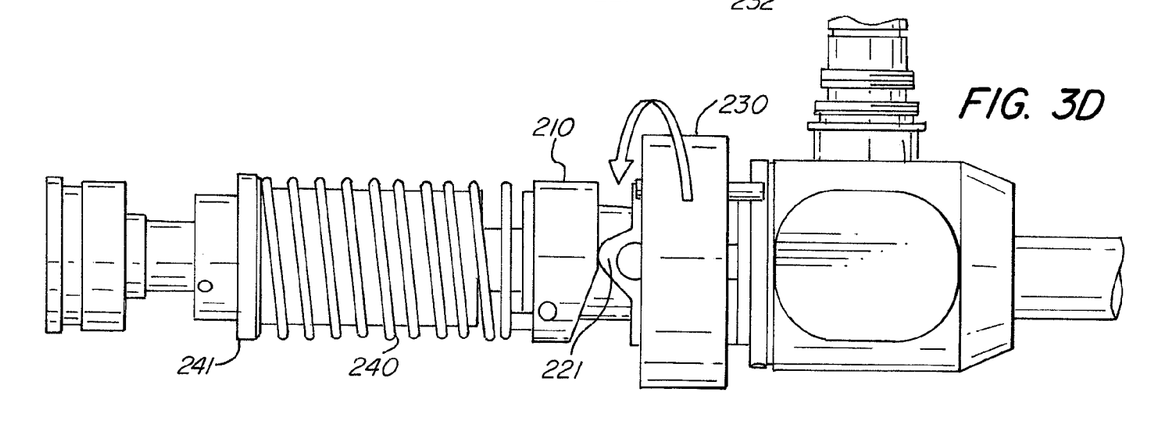
FIG. 3D is another side view of the proximal end of the swing prism endoscope of the present invention with the portion of the endoscope forming the handle removed.

In order to improve the ability of a surgeon to accurately adjust the viewing angle of the swing prism, it is preferable that the rotation of the adjusting knob 230 have a 1:1 correspondence with the change in the viewing angle of the prism, i.e. when the knob is rotated 30 degrees, the viewing angle of the swing prism is changed 30 degrees. This can be achieved by choosing the appropriate combination of prism reflectance angle and the slope of the sloped transition region 214. The surgeon's manipulation of the swing prism can further be enhanced by the use of indicia on endoscope 100 that will inform the surgeon of the current view angle of the prism. For instance, FIG. 3B illustrates a mechanism by which the surgeon can determine if the prism is disposed in standard preset position. In this embodiment, a portion of the housing of endoscope 100 comprises pairs of dimples 234 that are adjacent to adjusting knob 230 and are positioned about the longitudinal axis 116 at standard endoscopic viewing angles, such as 0, 30, 45, 70, 90, or 120 degrees. A rod 232 is coupled to adjusting knob 230 and extends in the distal direction over the portion of the housing comprising dimples 234. As the adjusting knob 230 rotates to change the prism viewing angle, the rod 232 rotates over the housing surface. When the rod 232 is positioned over a standard viewing angle, the rod is received and secured between a pair of dimples. The use of dimples 234 enables a surgeon to visually and through feel determine when the swing prism is positioned at a standard viewing angle. Alternatively, dimples 234 can be replaced by dents that recede into the surface of the housing and receive rod 232. The advantage of preset positions is that a surgeon can have the viewing angle set to a preset position and feel comfortable that the endoscopic viewing angle is exactly at a desired angle, such as 30 degrees. As noted above, surgeons rely heavily on knowing that a certain endoscope is a "30" or a "45", and they know what the anatomy should look like given a certain scope. The present endoscope provides surgeons with the simplicity of a single endoscope with variable direction of view and at the same time enables the surgeon to be certain of the viewing angle that the endoscope is set to.

The present invention has been described above in terms of a presently preferred embodiment so that an understanding of the present invention can be conveyed. However, many alternative designs and structural arrangements are possible without departing from the principle of the invention. The scope of the present invention should therefore not be limited by the embodiments illustrated, but rather it should be understood that the present invention has wide applicability with respect to multi-directional viewing instruments. All modifications, variations, or equivalent elements and implementations that are within the scope of the appended claims should therefore be considered within the scope of the invention.

What is claimed is:

1. A swing prism endoscope comprising:
    an endoscope shaft, the endoscope shaft having a proximal end and a distal end, and a longitudinal axis that runs from the proximal end to the distal end;
    a swing prism mounted to the distal end of the endoscope shaft, the swing prism configured to rotate substantially between zero and 60 degrees relative to the longitudinal axis of the endoscope shaft, such that a viewing angle of the endoscope is altered substantially between zero and 120 degrees relative to the longitudinal axis of the endoscope shaft;
    a control element having an annular portion that extends about the longitudinal axis of the endoscope shaft, the annular portion of the control element extending in a direction parallel to the longitudinal axis of the endoscope shaft between a proximal surface of the control element and an opposing variable control surface of the control element, the variable control surface having a trough portion and a peak portion, the variable control surface and the trough portion and the peak portion all being oriented in a distal direction along the longitudinal axis towards the distal end of the endoscope;
    a drive element positioned distally relative to the annular portion of the control element, the drive element configured to rotate about a longitudinal axis of the endoscope, the drive element including an engaging element that contacts the variable control surface of the annular portion of the control element and moves relative to the variable control surface while contacting the variable control surface, causing the annular portion of the control element to be displaced in an axial direction of the longitudinal axis of the endoscope shaft, the engaging element being oriented in a proximal direction along the longitudinal axis towards the proximal end of the endoscope; and
    a prism adjusting knob, the prism adjusting knob located external to the endoscope shaft, the movement of the prism adjusting knob causing the engaging element to correspond to the variable control surface, the engaging element sliding along the variable control surface, the prism adjusting knob being located distally along the longitudinal axis relative to the annular portion of the control element and the engaging element, such that the prism adjusting knob does not circumferentially encompass the engaging element;
    wherein when the engaging element slides toward the peak portion of the variable control surface, the annular portion of the control element is displaced towards the proximal end of the endoscope shaft, and when the engaging element slides towards the trough portion of the variable control surface, the annular portion of the control element is displaced towards the distal end of the endoscope shaft.

2. The endoscope of claim 1, further comprising a sloped transition region extending from the trough portion to the peak portion.

3. The endoscope of claim 1, further comprising a wire, wherein the annular portion of the control element displaces the wire axially along the longitudinal axis of the endoscope, the wire being coupled to the swing prism at one end of the wire and to the annular portion of the control element at the other end of the wire, such that the axial displacement of the wire induces the swing prism to rotate about a prism axis to alter the viewing angle of the endoscope between forward and side directions.

4. The endoscope of claim 1, wherein, during operation of the endoscope, the annular portion of the control element maintains its orientation relative to the longitudinal axis of the endoscope during axial displacement of the annular portion of the control element by not rotating during axial displacement relative to the longitudinal axis of the endoscope.

5. The endoscope of claim 1, wherein the viewing angle of the endoscope is changeable without altering the orientation of the endoscope within the body cavity.

6. The endoscope of claim 1, wherein the prism adjusting knob is magnetically coupled to the engaging element.

7. The endoscope of claim 1, wherein the prism adjusting knob is radially disposed above at least one of the engaging element and the variable control surface, and rotates about the longitudinal axis of the endoscope.

8. The endoscope of claim 1, further comprising a spring configured to engage the annular portion of the control element so as to force the variable control surface to contact the engaging element.

9. The endoscope of claim 8, wherein the spring resides between the annular portion of the control element and a spring retaining element.

10. The endoscope of claim 1, wherein the rotation of the prism adjusting knob induces a corresponding rotation of either the engaging element or control surface, wherein the rotation of the knob has a 1:1 correspondence to the change of the viewing angle of the swing prism.

11. The endoscope of claim 1, wherein the endoscope comprises at least one preset viewing angle such that when the prism adjusting knob is rotated to the preset viewing angle, the prism adjusting knob is secured at that location.

12. The endoscope of claim 1, wherein the prism adjusting knob includes an orientation element that extends along the longitudinal axis of the endoscope and engages a portion of the endoscope shaft that encompasses the longitudinal axis of the endoscope; and
wherein the endoscope shaft includes a receiving element at the preset viewing angle that receives and secures the orientation element at that location.

13. The endoscope of claim 12, wherein the receiving element is one or more dimples or dents.

14. The endoscope of claim 12, wherein the orientation element is a rod.

15. The endoscope of claim 1, wherein when the swing prism is oriented with a viewing angle in the forward direction, the swing prism conveys a light image to transmittal optics or a solid state imager without substantially altering the course of the light image transmitted to the transmittal optics or the solid state imager.

16. The endoscope of claim 1, wherein when the swing prism is oriented with a viewing angle in the side direction, the swing prism reflects a light image to transmittal optics or a solid state imager by altering the course of the light image transmitted to the transmittal optics or the solid state imager from a first direction to a second direction.

17. The endoscope of claim 1, wherein the swing prism is a dove prism.

18. The endoscope of claim 1, wherein the swing prism is disposed within a housing that comprises a viewing window that spans the forward and side view angles.

19. The endoscope of claim 18, wherein the portion of the viewing window that spans the forward and side view angles comprises a spherical arc.

20. The endoscope of claim 1, further comprising a handle that encompasses the longitudinal axis of the endoscope that is adjacent to the prism adjusting knob such that the endoscope can be grasped and the prism adjusting knob rotated with a single hand.

21. The endoscope of claim 20, wherein the handle and the prism adjusting knob are adjacent to one another.

22. The endoscope of claim 1, further comprising indicia on the endoscope that informs a surgeon of the current view angle of the prism.

23. The endoscope of claim 1, wherein the distal end of the housing incorporates a cavity that receives the prism and is characterized by a curved surface, which is in the form of a spherical arc and a ledge that receives a corresponding curved viewing window.

24. The endoscope of claim 23, wherein the viewing window is spherically shaped.

25. The swing prism endoscope of claim 1, wherein the rotation of the swing prism alters the viewing angle of endoscope between forward, side and backward directions.

26. The endoscope of claim 1, wherein the prism adjusting knob is magnetically coupled to the drive element.

27. The endoscope of claim 26, wherein the prism adjusting knob and/or the drive element includes a magnetic element.

28. The endoscope of claim 1, wherein the peak corresponds to a maximum viewing angle of the swing prism and the trough corresponds to a minimum viewing angle of the swing prism.

29. The endoscope of claim 1, wherein the prism adjusting knob does not circumferentially encompass the annular portion of the control element.

30. A swing prism endoscope comprising:
an endoscope shaft, the endoscope shaft having a proximal end and a distal end, and a longitudinal axis that runs from the proximal end to the distal end;
a handle that encompasses the longitudinal axis of the endoscope;
a swing prism mounted to the distal end of the endoscope shaft, the swing prism configured to rotate substantially between zero and 60 degrees relative to the longitudinal axis of the endoscope shaft, such that a viewing angle of the endoscope is altered substantially between zero and 120 degrees relative to the longitudinal axis of the endoscope shaft;
a control element, including an annular portion that extends about the longitudinal axis of the endoscope shaft, the annular portion of the control element extending in a direction parallel to the longitudinal axis of the endoscope shaft between a proximal surface of the control element and an opposing variable control surface of the control element, the variable control surface having a trough portion, a peak portion and a sloped transition region extending from the trough portion to the peak portion, the variable control surface, the trough portion, the peak portion and the sloped transition region all being oriented in a distal direction along the longitudinal axis towards the distal end of the endoscope;
a drive element positioned distally relative to the annular portion of the control element, the drive element configured to rotate about a longitudinal axis of the endoscope, the drive element including an engaging element that is moveable relative to the variable control surface while contacting the variable control surface, causing the control element to be displaced in an axial direction of the longitudinal axis of the endoscope shaft, the engaging element being oriented in a proximal direction along the longitudinal axis towards the proximal end of the endoscope; and
a prism adjusting knob encompassing the drive element, the prism adjusting knob located external to the endoscope shaft, the movement of the prism adjusting knob causing the engaging element to correspond to the variable control surface, the engaging element sliding along the variable surface, the prism adjusting knob being located distally along the longitudinal axis relative to the annular portion of the control element and the engaging element, such that the prism adjusting knob does not circumferentially encompass the engaging element;

wherein when the engaging element slides toward the peak portion of the variable control surface, the annular portion of the control element is displaced towards the proximal end of the endoscope shaft and when the engaging element slides towards the trough portion of the variable control surface, the annular portion of the control element is displaced towards the distal end of the endoscope shaft.

31. The endoscope of claim 30, wherein the prism adjusting knob does not circumferentially encompass the annular portion of the control element.

* * * * *